(12) United States Patent
Fu et al.

(10) Patent No.: US 8,663,677 B2
(45) Date of Patent: Mar. 4, 2014

(54) CONTROLLED RELEASE SYSTEM AND MANUFACTURING METHOD THEREOF

(75) Inventors: Yin-Chih Fu, Kaohsiung (TW); Chih-Kuang Wang, Hsinchu (TW); Gwo-Jaw Wang, Taipei (TW); Mei-Ling Ho, Kaohsiung (TW); Hui-Ting Chen, Yonghe (TW); Je-Ken Chang, Kaohsiung (TW); Cherng-Chyi Tzeng, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 13/209,213

(22) Filed: Aug. 12, 2011

(65) Prior Publication Data
US 2011/0312885 A1 Dec. 22, 2011

Related U.S. Application Data

(63) Continuation-in-part of application No. 11/902,312, filed on Sep. 20, 2007, now abandoned.

(30) Foreign Application Priority Data

Mar. 8, 2007 (TW) .............................. 96108002 A

(51) Int. Cl.
*A61K 38/18* (2006.01)
*A61K 31/7088* (2006.01)
*A61K 47/04* (2006.01)
*A61K 38/00* (2006.01)

(52) U.S. Cl.
USPC .............. 424/426; 514/7.6; 514/1.1; 514/770

(58) Field of Classification Search
None
See application file for complete search history.

(56) References Cited

U.S. PATENT DOCUMENTS

| 6,270,700 | B1 | 8/2001 | Ignatious | |
| 7,211,275 | B2 * | 5/2007 | Ying et al | ..................... 424/462 |
| 2008/0131478 | A1 * | 6/2008 | Schwendeman et al. | ..... 424/424 |
| 2011/0052691 | A1 * | 3/2011 | Fu et al. | ....................... 424/484 |

OTHER PUBLICATIONS

Pluronic F68 Block Copolymer Surfactant BASF Corporation 2004.*
Pluronic F127 Block Copolymer Surfactant BASF Corporation 2002.*
Wang et al. "Controlled release of rhBMP-2 carriers in the regeneration of osteonecrotic bone" Bimaterials 30 (2009) pp. 4178-4186.*
Yasuaki Ogawa et al, Chem. Pharm. Bull. 36, A New Technique to Efficiently Entrap Leuprolide Acetate into Microcapsules of Polylactic Acid or Copoly(Lactic/Glycolic) Acid. 1998, pp. 1095-1103.
Chih-Kuang Wang et al, Diomaterials 30. Controlled-release of rhBMP-2 Carriers in the Regeneration of Osteonecrotic Bone, May 17, 2009, pp. 4178-4186.

* cited by examiner

*Primary Examiner* — Robert A Wax
*Assistant Examiner* — Danah Al-Awadi
(74) *Attorney, Agent, or Firm* — Muncy, Geissler, Olds & Lowe, P.C.

(57) ABSTRACT

A controlled release system and manufacturing method is provided. The method comprises providing a first aqueous solution containing a hydrophilic drug and an alkaline agent, providing an organic solution containing a hydrophobic molecule, providing a second aqueous solution containing a hydrophilic surfactant, mixing the first hydrophilic solution with the organic solution to form a first emulsion, and mixing the first emulsion with a second aqueous solution to form a second emulsion containing delayed-release microsphere.

20 Claims, 24 Drawing Sheets
(14 of 24 Drawing Sheet(s) Filed in Color)

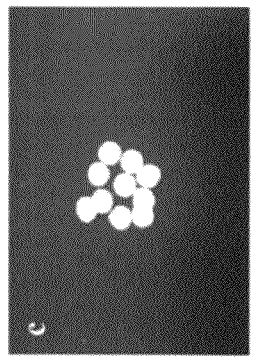
FIG. 11c
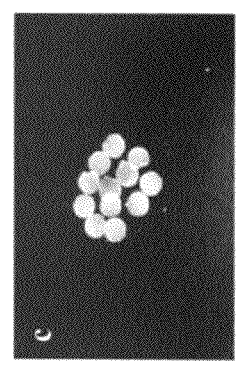
FIG. 12c
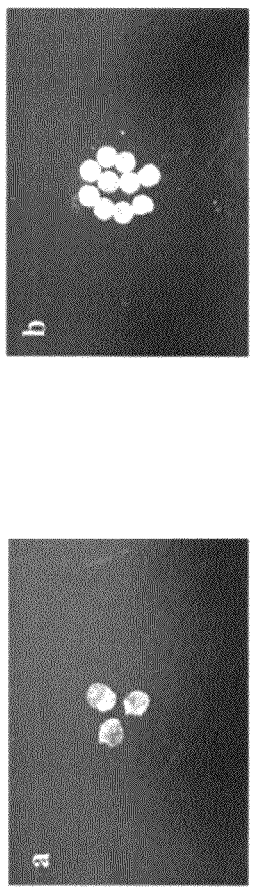
FIG. 11b
FIG. 11a
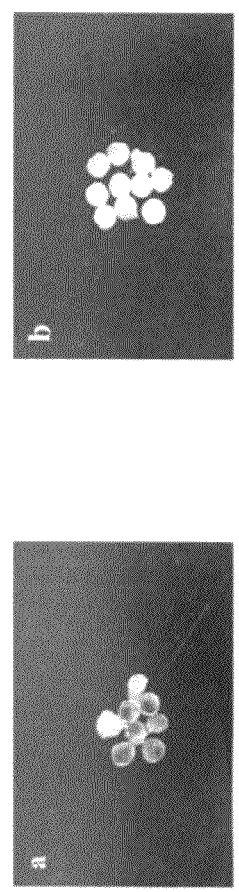
FIG. 12b
FIG. 12a

CONTROLLED RELEASE SYSTEM AND MANUFACTURING METHOD THEREOF

CROSS REFERENCE TO RELATED APPLICATION

This application is a Continuation-in-Part of co-pending application. No. 11/902,312, filed on Sep. 20, 2007, and for which priority is claimed under 35 U.S.C. §102, the entire contents of which are hereby incorporated by reference.

BACKGROUND OF THE INVENTION

1. Field of the Invention

The invention relates to controlled release systems, and in particular to double emulsion carriers containing alkaline compound.

2. Description of the Related Art

The desirability of coating medical devices such as, inter alia, surgical implants, sutures and wound dressings with pharmaceutical agents is well known. Such coated devices provide a means for locally delivering pharmaceutical or therapeutic agents at the site of medical intervention to treat a variety of diseases. For example, surgical implants or sutures coated with antibiotics can provide local delivery of antibiotic directly to an implantation or suture site, thereby decreasing the onset of infection following the surgical intervention.

Thus, there is an increasing interest in developing a drug delivery system which is both safe and which provides a high biological availability of the drug, i.e. to maximize pharmaceutical activity of known drugs as well as to minimize the side effects thereof. Due to their uniform release rate during a given time period and the non-toxic property of degradation products, biodegradable polymers have been widely investigated as drug carriers. Biodegradable polymer drug carriers are especially useful for delivering drugs requiring continuous and sustained release with a single bolus administration, e.g. peptide or protein drugs, which should be administered daily because of quick loss of activity in the body.

Aliphatic polyesters, such as poly(lactic acid) (PLA), poly(glycolic acid) (PGA), copolymers of PLA and PGA (PLGA) or poly(carprolactone) (PCL), and polyanhydrides have been widely used for biodegradable polymers. They can be formulated as various shapes, such as films, strips, fibers, gels or microspheres, and the physiologically active agents are incorporated into the formulations and administered intramuscularly or subcutaneously. However, microspheres have been a particularly preferred formulation because the drug release rate can be easily controlled and the small microsphere particle sizes of 1~500 μm enables direct injection into the body by conventional methods. Preparation methods, however, to achieve uniform particle size of the microspheres and effective loading of drugs are still under investigation.

Microspheres have been prepared by various methods such as emulsion solvent evaporation, phase separation, spray-drying, or solvent extraction. However, improved methods for preparing microspheres having uniform particle size and effective drug loading are desirable. According to the emulsion solvent evaporation method, a hydrophobic polymer is dissolved in a water-immiscible organic solvent, such as dichloromethane, chloroform, or ethyl acetate, to give a polymer solution. Then, a physiologically active agent is dissolved or suspended in the polymer solution. The resulting solution is added into an aqueous solution of a surfactant to form an emulsion system, and microspheres are obtained by evaporating the solvent under vacuum or heating. Although this method is useful for very poorly water-soluble drugs it has very low loading efficiency for water-soluble drugs.

Ogawa et al. (Chem. Pharm. Bull., 1988: 36: p 1095-1103) disclose a w/o/w double emulsion method for incorporating a water-soluble drug into microspheres. Accordingly, a biodegradable polymer is dissolved in a water-immiscible organic solvent to give a polymer solution, and a water-soluble physiologically active agent is emulsified into the polymer solution to give a w/o emulsion system. This emulsion is emulsified again into an aqueous solution of a surfactant to produce the w/o/w double emulsion system. The microspheres containing the water-soluble physiologically active agent are obtained by evaporating the solvent. This method requires use of gelatin to increase the viscosity of the w/o emulsion and the loading efficiency decreases remarkably because the particle size of the microsphere is less than 10 .mu.m.

Additionally, a solid/oil/water (s/o/w) double emulsion method has been developed. In this method, proteins or drugs are freeze-dried to form a solid material, and encapsulated to a solid/oil/water (s/o/w) form. However, the protein drug without protection easily loses activity because the protein drug exists in an organic solvent by the solid form and proceeded with a freeze-dried procession. In addition, the solid-form complex is difficult to disperse into the first emulsion.

Thus, there is no currently available method or composition that can carry and protect sensitive drugs, specifically water-soluble drugs such as peptide, protein and nucleic acid. Furthermore, the hydrolysis of biodegradable material may decrease the pH of the biological subject, thus adversely affecting cell growth. To overcome the above problems, a controlled release system having a stable pH, effective carriage and protection of sensitive drug and a slow release rate is needed.

BRIEF SUMMARY OF INVENTION

The invention provides a controlled release system to protect sensitive drugs, comprising an alkaline material, with slow release rate and stable pH value.

The invention also provides a method of manufacturing controlled release system comprising providing a first aqueous solution containing a hydrophilic drug and an alkaline agent, providing an organic solution containing a hydrophobic molecule, or adding hydrophobic surfactant again, providing a second aqueous solution containing a hydrophilic surfactant, mixing the first hydrophilic solution with the organic solution to form a first emulsion, and mixing the first emulsion with a second aqueous solution to form a second emulsion containing delayed-release microsphere.

The invention further provides a controlled release system prepared by the disclosed method, wherein the controlled release system has a pH between about 6.5 and 8.5, and a drug encapsulation rate exceeding 80%.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the office upon request and payment of the necessary fee.

The present invention will become more fully understood from the subsequent detailed description and the accompanying drawings, which are given by way of illustration only, and thus are not limitative of the present invention, and wherein:

FIGS. 11a-11c show the PLGA(50/50):HAp sample of Example 6 of the invention;

FIGS. 12a-12c show the PLGA(65/35):HAp sample of Example 6 of the invention;

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The invention provides a method for manufacturing a controlled release system. The method comprises providing a hydrophilic drug containing an alkaline material, and mixing the hydrophilic drug with an organic solution to form a first emulsion.

Figure 25:
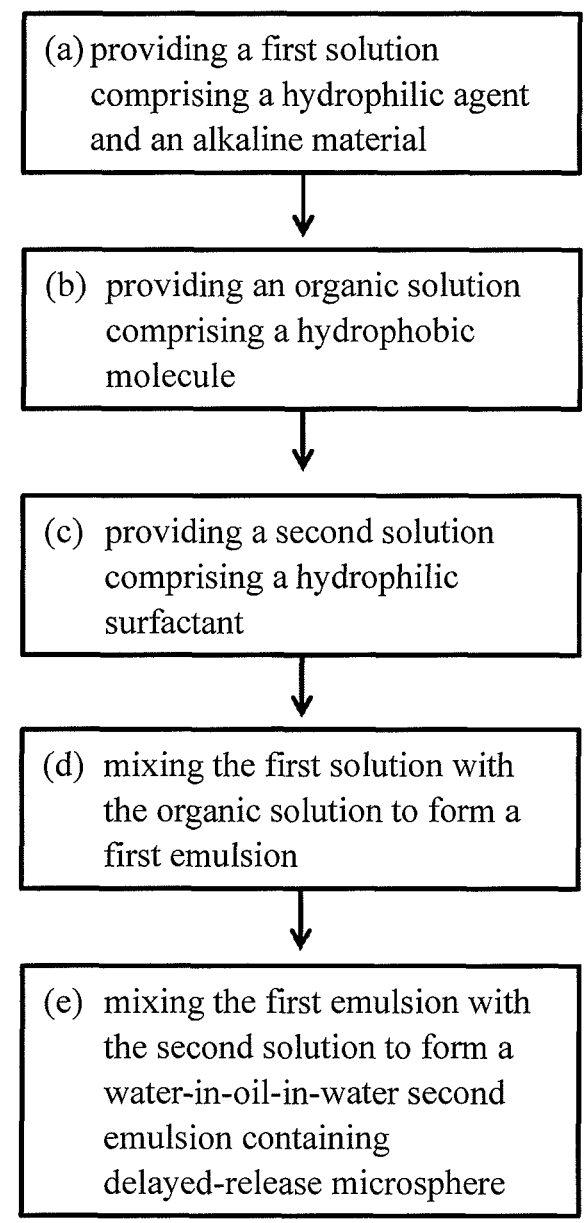
FIG. 25 shows a flowchart of a method for manufacturing a controlled release system of the invention.

The invention provides a method for manufacturing a controlled release system, comprising (a) providing a first solution comprising a hydrophilic agent and an alkaline material, wherein the alkaline material comprises hydroxyapatite, tircalcium phosphate, bioglass, calcium carbonate, polyamidoamine (PAMAM) dendrimer, xyllitol, or combinations thereof;

(b) providing an organic solution comprising a hydrophobic molecule;

(c) providing a second solution comprising a hydrophilic surfactant;

(d) mixing the first solution with the organic solution to form a first emulsion; and (e) mixing the first emulsion with the second solution to form a water-in-oil-in-water second emulsion containing delayed-release microsphere;

and provided that there is no isolating precipitation between step (a) and step (b) (FIG. 25).

Figure 1:
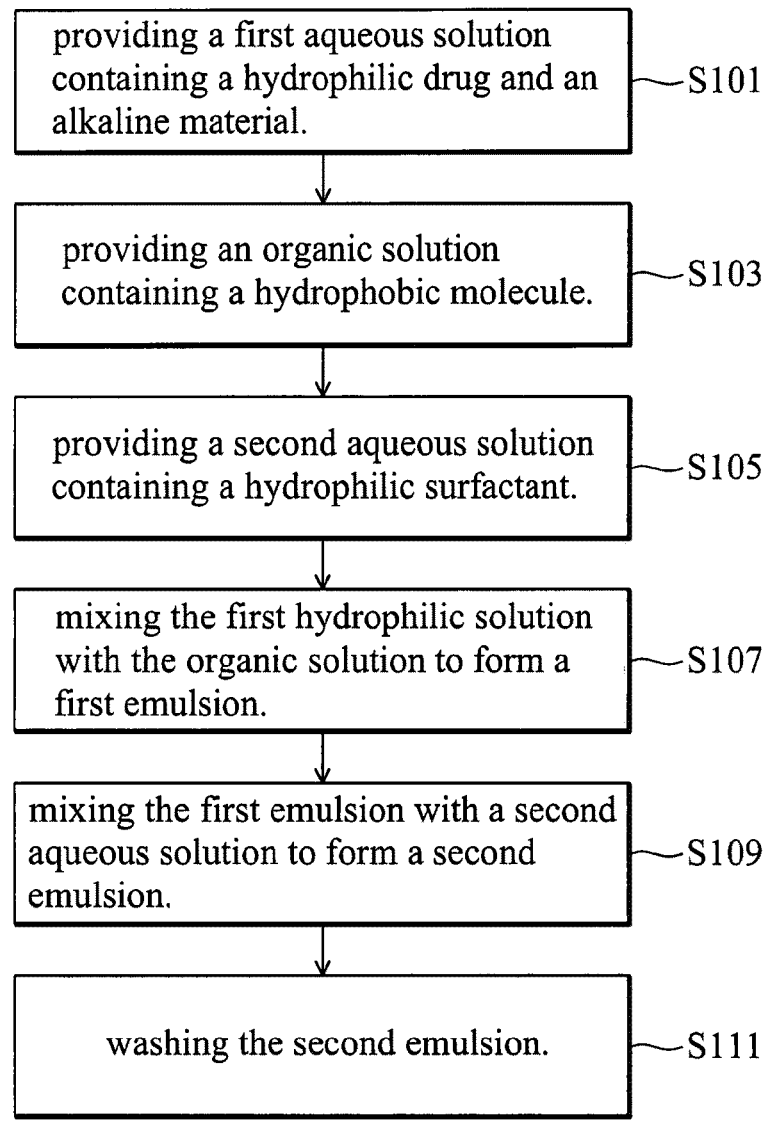
FIG. 1 is a flowchart of a method for manufacturing a controlled release system of the invention.

Referring to FIG. 1, in step S101, a first solution including a hydrophilic drug and an alkaline material is provided. The hydrophilic drug has a bioactivity, can be used to treat or protect a biological subject. The hydrophilic drug includes, but are not limited to, protein drug (such as peptide, enzyme, or nucleic acid), antibiotic (such as penicillin, cephalosprins, vancomycin hydrochloride, or lincomycin), or growth factor (such as bone morphogenetic proteins, TGF-β1, fibroblast growth factors, platelet-derived growth factor, or insulin-like growth factor).

Additionally, the first solution contains at least one alkaline material, having pH between about 7.4 and 14, preferably, about 7.4 and 10.4. Conventionally, the pH of the biological subject is decreased when the biodegradable is hydrolyzed therein. However, the alkaline material of the invention stabilizes the pH in the biological subject, maintained at about 6.5 to 8.0. The alkaline material can include, but is not limited to, hydroxyapatite, tircalcium phosphate, bioglass, calcium carbonate, polyamidoamine (PAMAM) dendrimer, xyllitol, or combinations thereof.

In an embodiment of the invention, an excipient is also added to the hydrophilic drug. The excipient can include, but is not limited to, dextrin, α,β-Trehalose, D-(+)-Trehalose, sucrose, glycerol, cyclodextrin, polyhydric alcohols, or PEG.

Referring to step S103, an organic solution containing a hydrophobic molecular and/or a hydrophobic surfactant is provided. The organic solutions can include, but is not limited to, dichloromethane, chloroform, ethyl acetate, 1,4-dioxane, dimethylformamide (DMF), dimethyl sulphoxide (DMSO), toluene, or THF, preferably, dichloromethane, or ethyl acetate. The hydrophobic molecule is degraded in the biological subject with no impact thereon. The hydrophobic molecule is a bio-molecule (biodegradable molecule), for example, phospholipids, lecithin, polylactic acid (PLA), polyglycolate, polylactide-co-glycolide (PLGA), polyglutamic acid, polycaprolactone (PCL), polyanhydrides, polyamino acid, polydioxanone, polyhydroxybutyrate, polyphophazenes, polyesterurethane, polycarbosyphenoxypropane-cosebacic acid, or polyorthosester, preferably, PLA, PLGA, PCL, or polyphophazenes.

The hydrophobic surfactant includes polyoxypropylene-polyoxyethylene copolymers, polysorbates, polyglycerol polyricinoleate, sorbitan tristearate, mono-diglycerides of fatty acid, polyglycerol state, sorbitan mono-stearate, sobitan mon-palmitate, sodium bis(2-ethylhexyl) sulfosuccinate (AOT), pluronic, span 83, or span 40, preferably, sorbitan mono-stearate, or polysorbates.

Referring to step S105, a second solution containing a hydrophilic surfactant is provided. The hydrophilic surfactant includes polyvinyl alcohol (PVA), NP-5, Triton x-100, Tween 40, PEG 200-800, sodium dodecyl sulfate (SDS), alcohol ethoxylates, alkylphenol ethoxylates, secondary alcohol ethoxylates, fatty acid ester, or alkyl polygylcosides, preferably, PVA, or Triton x-100.

Referring to step S107, the first solution and organic solution are mixed to form a first emulsion. The ratio of hydrophilic drug to the organic solution is 1:5 to 1:13, preferably, 1:7 to 1:10. The first emulsion is accomplished by a powerful engineering force. The first solution and organic solution can be completely emulsified to form the first emulsion by homogenizer, supersonic oscillator, oscillator, magnetic stir reactor, or motor reactor. For example, the rotation rate is about 800 to 1500 rpm, preferably, about 900 to 1300 rpm, the stirring time is about 2 to 30 min, preferably, about 10 to 20 min if a magnetic stir reactor is used.

Referring to step S109, the first emulsion and the second solution are mixed to form a second emulsion. The second emulsifying is accomplished by a weak engineering force. The first emulsion and the second emulsion containing hydrophilic surfactant can be completely emulsified by magnetic stir reactor, or motor reactor to form the second emulsion (w/o/w). For example, the rotation rate is about 300 to 1000 rpm, preferably, about 400 to 800 rpm, the stirring time is about 1 to 24 hours, preferably, about 4 to 12 hours if the magnetic stir reactor is used.

Referring to step S111, the second emulsion is washed to form the controlled release system of the invention. The emulsion is washed 2 to 3 times for 2 to 5 min each with water. The temperature of steps S101 to S111 is controlled in 0 to 60° C.

The pH of the controlled release system of the invention is about 6.5 to 8.5, preferably, about 7 to 8 when the controlled release system is dissolved in a physiological solution in vitro for one month. The drug encapsulation rate of the controlled release system exceeds 80%, and preferably, 90%. The controlled release system has a diameter of about 0.1 to 500 μm, preferably, about 1 to 150 μm. The burst release rate of the controlled release system at first hour is about 5% to 60%, preferably, about 15% to 50%, and the drug of the 80% is released during about 1 to 6 weeks, preferably, about 2 to 3 weeks. Additionally, the appearance and the capsulated drug of the controlled release system can be randomly changed.

In another embodiment of the invention, a mold is filled with the second emulsion to form a bone scaffold, the structure of which is not limited. The pH of the bone scaffold dissolved in a physiological solution in vitro for one month is about 6.5 to 8.5, preferably, about 7 to 8. The bone scaffold also can capsulate the drugs or bioactive molecules, and the drug encapsulation rate exceeds 80%, and, preferably, 90%. The burst release rate of the controlled release system at first hour is about 5% to 60%, preferably, about 15% to 50%, and the drug of the 80% is released during 1 to 6 weeks, preferably, 2 to 3 weeks. Additionally, the appearance and the capsulated drug of the controlled release system can be randomly changed.

EXAMPLES

Example 1

0% (span83)-0.1% (PVA)-10% (PLAG(65/35))-0 mg(HAP)

Figure 2A:
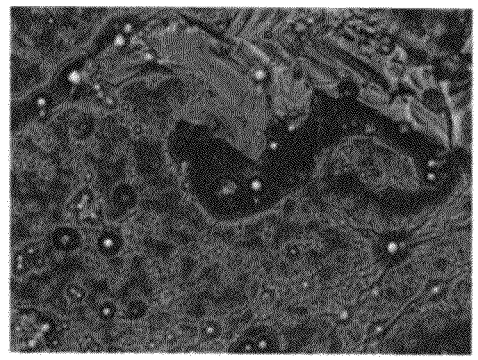
FIGS. 2a-2b are SEM and fluorescence microscopy images of Example 1 of the invention.
Figure 2B:
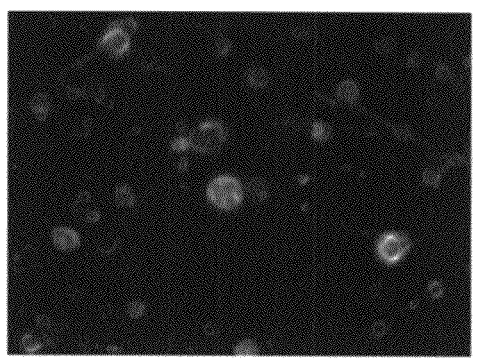

25 mg of bovine serum albumin (BSA) or 1 mg of fluorescein isothiocyanate-conjugated bovine serum albumin (FITC-BSA) and 250 μl of PBS were stirred for 5 min by oscillator to form a BSA/PBS solution (or FITC-BSA/PBS). The 0.25 g of PLGA dissolved in the 2.5 ml of dichloromethane to form a 10% PLGA solution. The BSA/PBS solution and PLGA solution were mixed at 1000 rpm for 15 min to form a first emulsion (w/o). The first emulsion (w/o) is added to 10 ml of 0.1% (w/v) PVA solution at 500 rpm for 5 min to form a second emulsion (w/o/w). After stirring for 4 hours and standing for 2 min, the supernatant of the second emulsion was obtained, and then centrifuged at 3000 rpm for 5 min to obtain a subphase solution. The subphase solution was again washed with ddH2O and centrifuged two times. The total subphase solutions were collected and free-dried to form the controlled release system of the invention. In this example, the rate of BSA encapsulation was 96 to 98%, and the rate of FITC-BSA encapsulation was 98 to 99%. FIG. 2a shows an image of the controlled release system of the invention from scanning electron microscopy (200×). FIG. 2b shows an image of the controlled release system from fluorescence microscopy.

Example 2

0% (span83)-0.1% (PVA)-10% (PLAG(65/35))-3.4 mg(HAp)

Figure 3A:
FIGS. 3a-3b are SEM and fluorescence microscopy images of Example 2 of the invention.
Figure 3B:
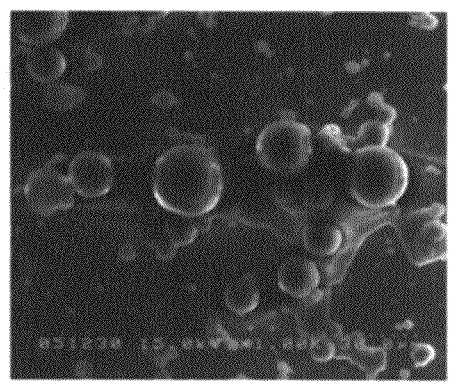
Figure 4A:
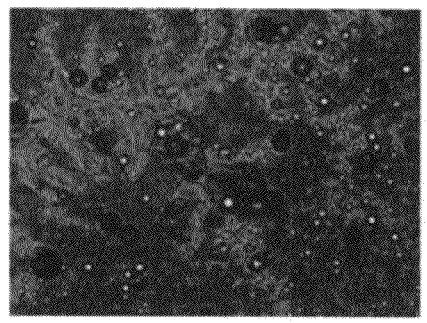
FIGS. 4a-4b are SEM images of Example 3 of the invention.
Figure 4B:
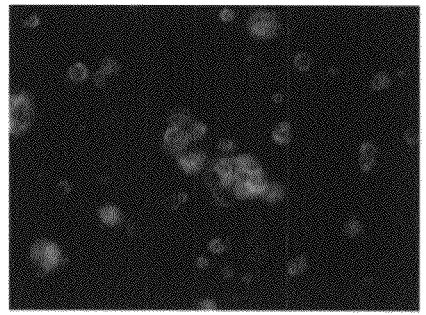

The same procedure carried out in Example 1 was repeated except that 3.4 mg of calcium phosphate tribase (HAp) was added. 1 g of the HAp (Alfa Aesar, AJahnson Matthey Company) was added to 10 ml PBS and mixed by supersonic oscillator for 10 min. After standing for 5 min, 250 μl of the supernatant (about 3.4 mg HAp) and 25 mg of BSA (or 1 mg of FITC-BSA) were mixed for 5 min to form BSA/HAp/PBS solution (or FITC-BSA/HAp/PBS). 0.25 g of PLGA were dissolved in 2.5 ml of dichloromethane to form a 10% PLGA solution. The BSA/PBS solution and PLGA solution were mixed with 1000 rpm for 15 min to form a first emulsion (w/o). The first emulsion (w/o) was added to 10 ml of 0.1% (w/v) PVA solution at 500 rpm for 5 min to form a second emulsion (w/o/w). After stirring for 4 hours and standing for 2 min, the supernatant of the second emulsion was centrifuged with 3000 rpm for 5 min to obtain a subphase solution. The subphase solution was again washed with ddH$_2$O and centrifuged two times. The total subphase solutions were collected and free-dried to form the controlled release system of the invention. In this example, the BSA encapsulation rate of the second emulsion was 96 to 99%, and the FITC-BSA encapsulation rate was 98 to 99%. FIG. 3a-3b shows the SEM images obtained at 200× magnification (FIG. 3a), 1000× magnification (FIG. 3b). FIG. 4a-4b shows the fluorescence microscopy images obtained at 200× magnification (FIG. 4a), and 1000× magnification (FIG. 4b).

Example 3

2% (span83)-0.1% (PVA)-10% (PLAG(65/35))-0 mg(HAp)

Figure 5A:
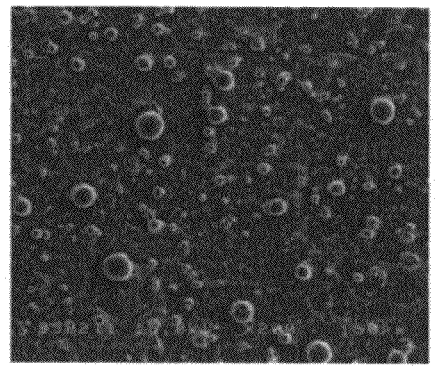
FIGS. 5a-5b are fluorescence microscopy images of Example 3 of the invention.
Figure 5B:
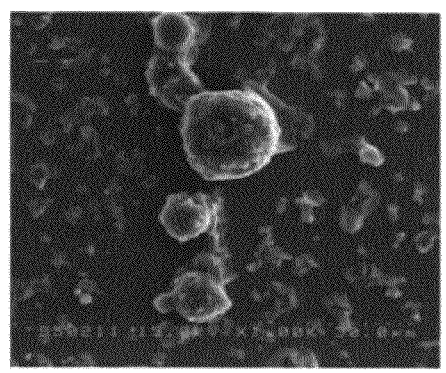
Figure 6A:
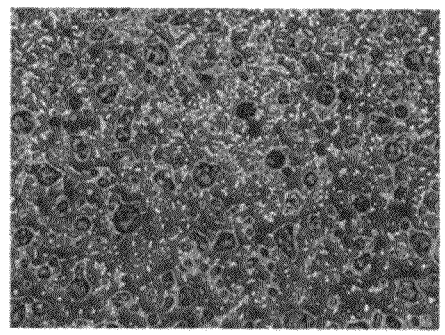
FIGS. 6a-6b are SEM images of Example 4 of the invention.
Figure 6B:
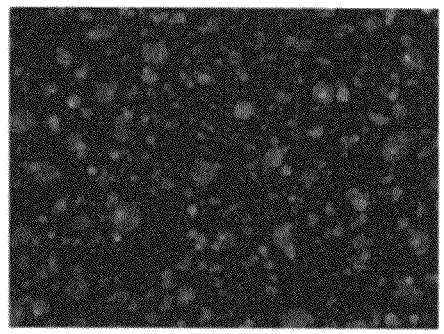

The same procedure carried out in Example 1 was repeated except that a 2% Span 83 hydrophobic surfactant was added to the 10% PLGA solution. In this example, the BSA encapsulation rate of the second emulsion was 97 to 99%, and the FITC-BSA encapsulation rate was 98 to 99%. Referring to FIG. 5a-5b, the second emulsion had a diameter below 50 μm. FIG. 5a is a SEM image of 200× magnification, and the FIG. 5b is a SEM image of 1000× magnification. FIG. 6a-6b show the fluorescence microscopy images obtained at 200× magnification (FIG. 6a), and 1000× magnification (FIG. 6b).

Example 4

2% (span83)-0.1% (PVA)-10% (PLAG(65/35))-3.4 mg(HAp)

Figure 7A:
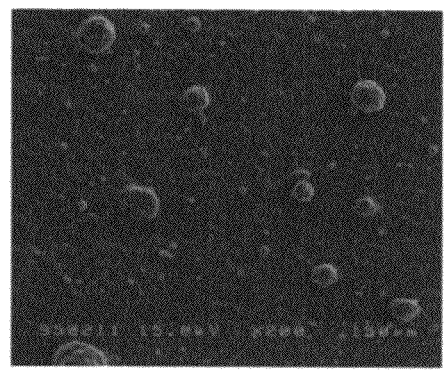
FIGS. 7a-7b are SEM images of Example 4 of the invention.
Figure 7B:
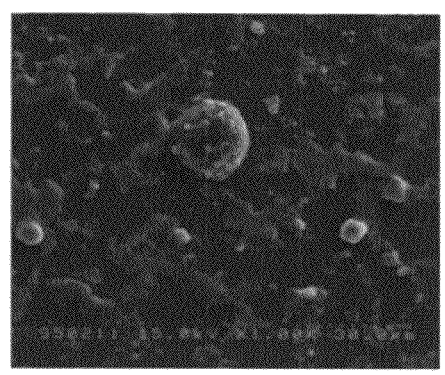
Figure 8A:
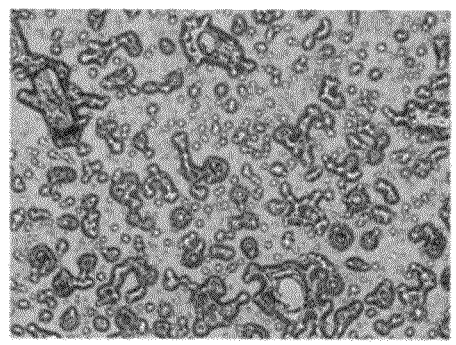
FIGS. 8a-8b are fluorescence microscopy images of Example 4 of the invention.
Figure 8B:
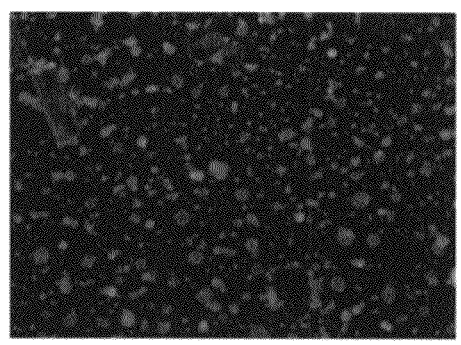

The same procedure carried out in Example 2 was repeated except that a 2% Span 83 hydrophobic surfactant was added to the 10% PLGA solution. In this example, the BSA encapsulation rate of the second emulsion was 98 to 99%, and the FITC-BSA encapsulation rate was 97 to 99%. FIG. 7a-7b are SEM images of the second emulsion obtained at 200× magnification (FIG. 7a), and 1000× magnification (FIG. 7b). FIG. 8a-8b are fluorescence microscopy images obtained at 200× magnification (FIG. 8a), and 1000× magnification (FIG. 8b).

Example 5

Figure 9A:
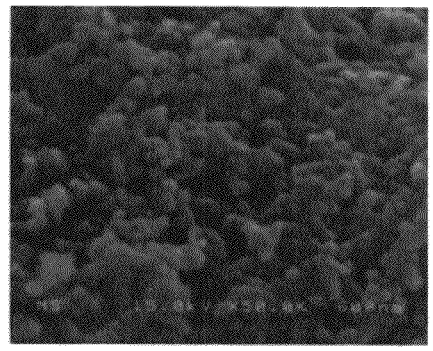
FIG. 9a shows the size of the commercial HAp.
Figure 9B:
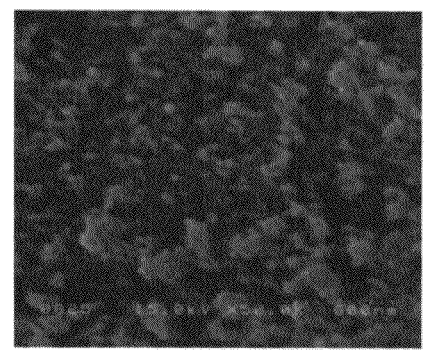
FIG. 9b shows the size of the self-made HAp.
Figure 10A:
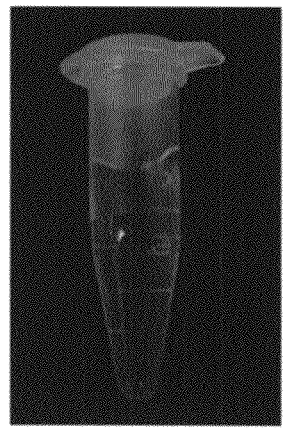
FIGS. 10a-10b shows HAp absorption of 95% of the FTI-BSA.
Figure 10B:
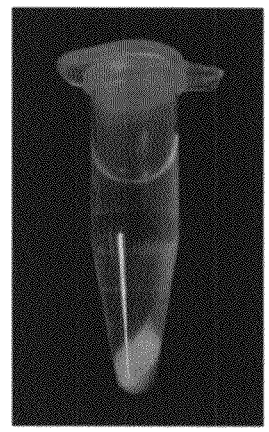

The Adsorption Experiment of the FITC-BSA and HAp 0.5 M of $Ca(OH)_2$ was heated at 37° C., 50 rpm for 30 min, and then the 0.5M of $H_3PO_4$ solution was added to the $Ca(OH)_2$ solution at a rate of 30-40 ml/min such that a ratio of Ca/P ration was 2.0. Additionally, the pH of the $Ca(OH)_2$ solution was adjusted to 10 by Tris-(hydroxymethyl)aminomethane buffer. Next, the $Ca(OH)_2$ solution was heated at 37° C. for 24 hours to form an educt, and then the educt was obtained by centrifugation at 3000 rpm and washed with dd$H_2O$ two times. Finally, the educt was free-dried to form the self-made HAp powder. Referring to FIG. 9a, the size of the commercial HAp (Alfa Aesar, A Johnson Matthey Company) was 0.1 μm. Referring to FIG. 9b, the size of the self-made HAp was 0.1 μm. Referring to FIG. 10a, under no HAp condition, the FITC-BSA produced no pellet by centrifugation at 6000 rpm. Referring to FIG. 10b, 95% of FTIC-BSA (1 mg) was absorbed by 32 mg of the commercial HAp. Additionally, the 8 mg, 16 mg, 20 mg, and 24 mg of the self-made HAp had an absorption rate of 24.78%, 65.85%, 70.48%, and 81.55% respectively.

Example 6

The pH of PLGA and HAp

Figure 13A:
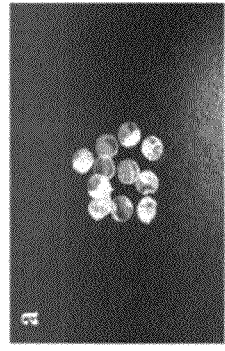
FIGS. 13a-13c show the PLGA(75/25):HAp sample of Example 6 of the invention.
Figure 13B:
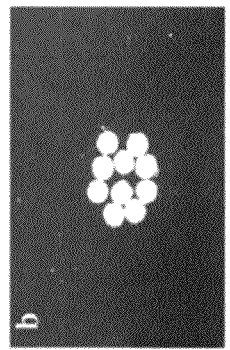
Figure 13C:
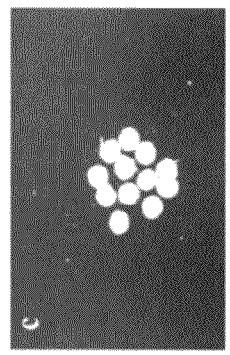
Figure 14A:
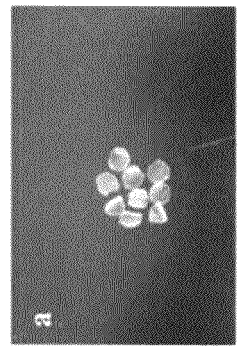
FIGS. 14a-14c show the PLGA(85/15):HAp sample of Example 6 of the invention.
Figure 14B:
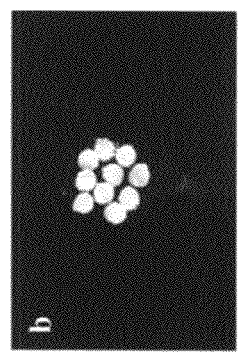
Figure 14C:
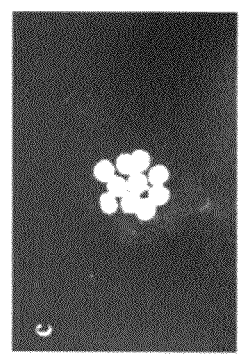
Figure 15A:
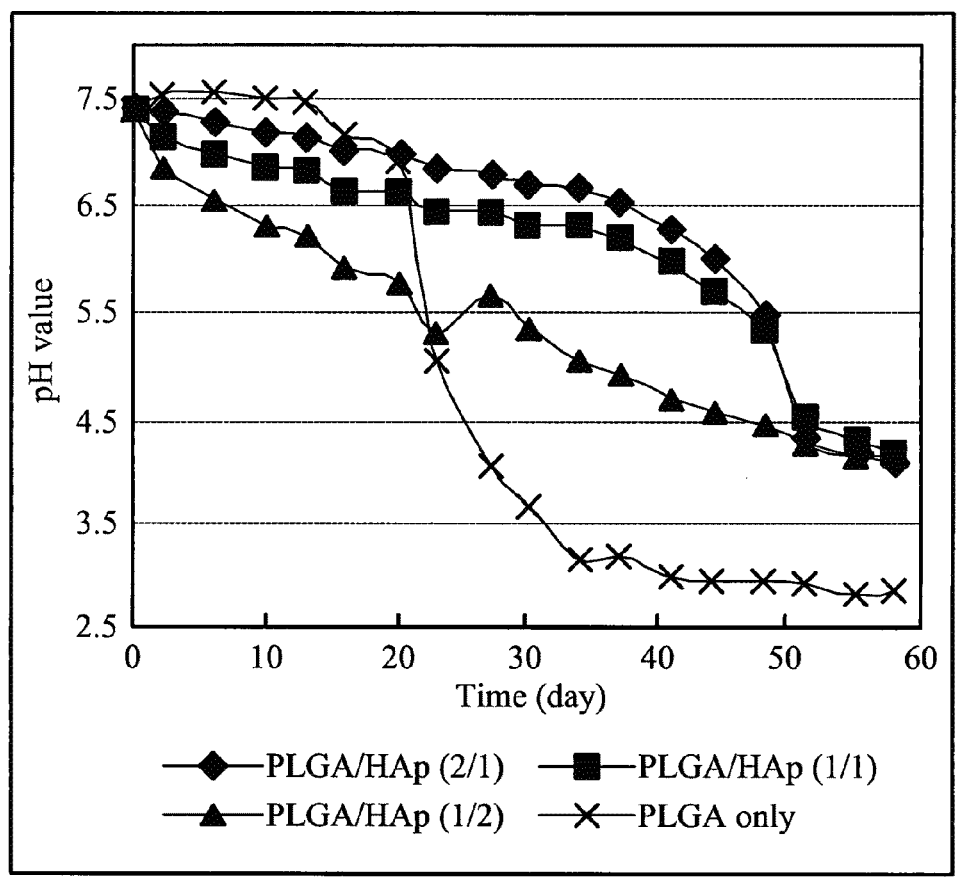
FIGS. 15a-15d show solution maintained at natural pH by HAp.
Figure 15B:
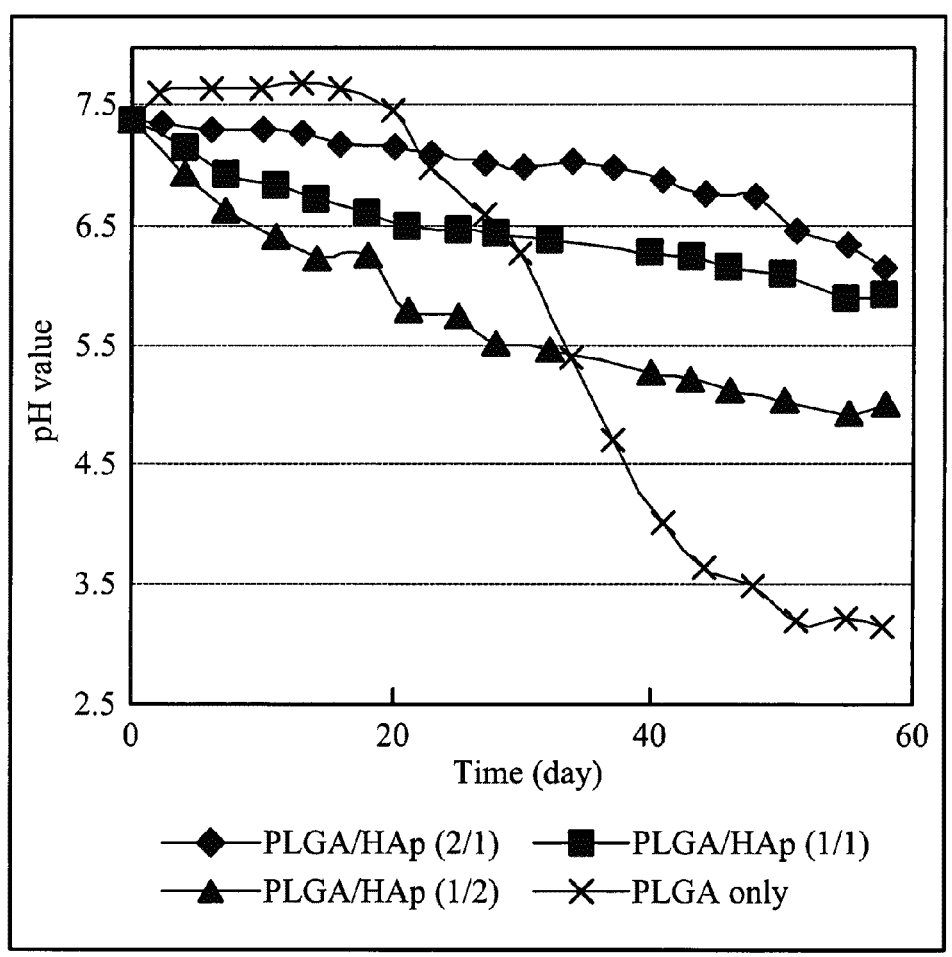
Figure 15C:
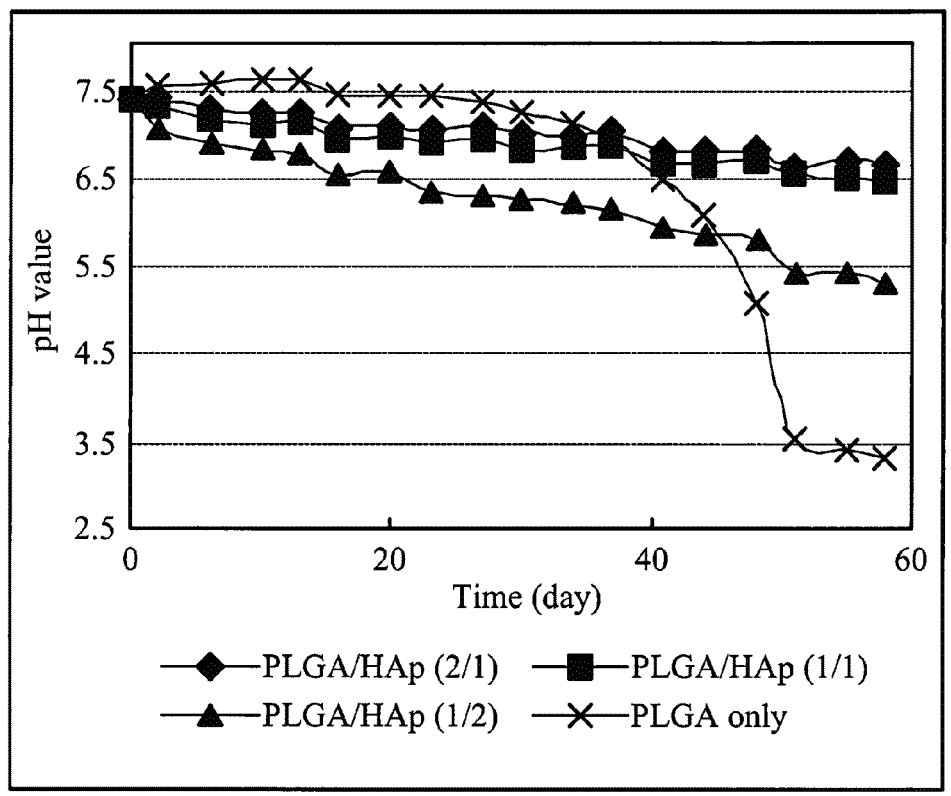
Figure 15D:
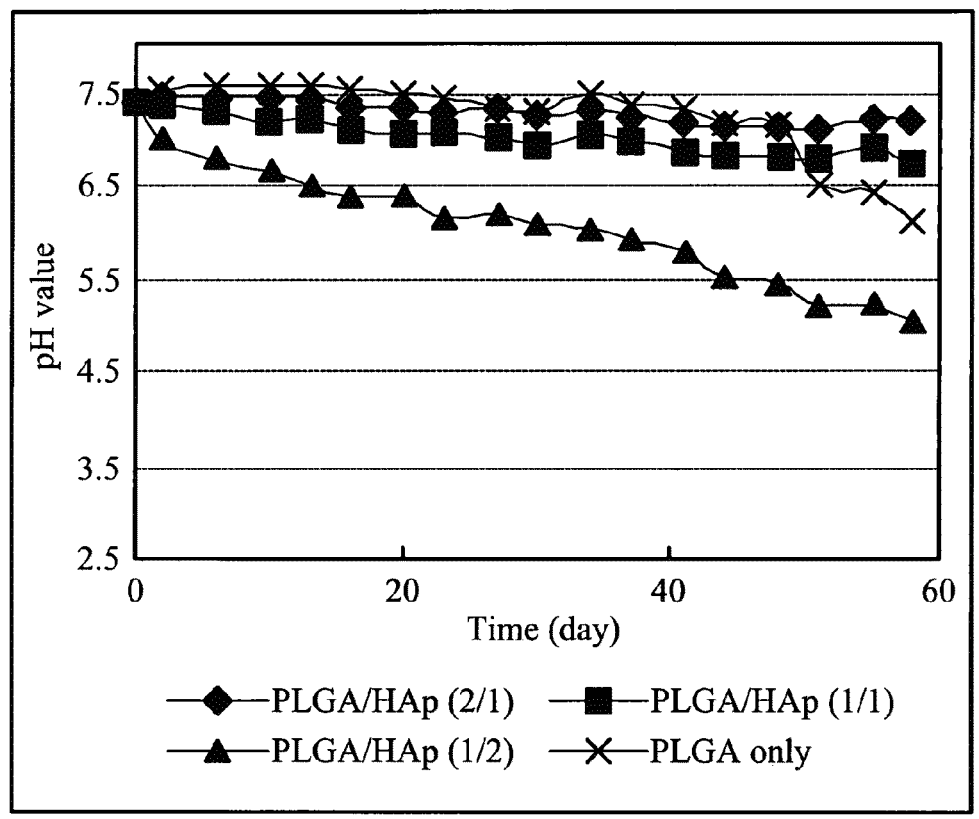

The various ratios of PLGA (85:15, 75:25, 65:35, and 50:50) were dissolved in the dichloromethane. 20 g of commercial HAp was dissolved in dd$H_2O$ with sonication for 15 min. After standing for 5 min, the upper ⅓ supernatant layer was obtained, and then the supernatant was free-dried to form the HAp powder. The HAp powder was added to the PLGA solution. The PLGA solution containing the HAp was added into a mold to form a sample, and then the organic solvent in this sample was removed. FIG. 11a-11c show samples of the PLGA(50/50) (FIG. 11a), PLGA(50/50)/HAp(1/1) (FIG. 11b), and PLGA(50/50)/HAp(1/1) (FIG. 11c) respectively. FIG. 12a-12c show samples of the PLGA(65/35) (FIG. 12a), PLGA(65/35)/HAp(1/1) (FIG. 12b), and PLGA(65/35)/HAp (1/1) (FIG. 12c) respectively. FIG. 13a-13c show samples of the PLGA(75/25) (FIG. 13a), PLGA(75/25)/HAp(1/1) (FIG. 13b), and PLGA(75/25)/HAp(1/1) (FIG. 13c) respectively. FIG. 14a-14c show samples of the PLGA(85/15) (FIG. 14a), PLGA(85/15)/HAp(1/1) (FIG. 14b), and PLGA(85/15)/HAp (1/1) (FIG. 14c) respectively. FIGS. 15a-15d show the samples maintained at a neutral pH for a long time by the PLGA containing HAp, and the maintained time was PLGA (85/15)>PLGA (85/15)>PLGA(75/25)>PLGA(50/50).

TABLE 1

| | the ratio of PLGA and HAp | | | | |
|---|---|---|---|---|---|
| | PLGA (50/50) | PLGA (65/35) | PLGA (75/25) | PLGA (85/15) | HAp only |
| HAp of 0 part | 0.0 mg | 0.0 mg | 0.0 mg | 0.0 mg | — |
| HAp of 0.5 part | 48.5 mg | 48.5 mg | 48.5 mg | 48.5 mg | — |
| HAp of 1 part | 91.5 mg | 91.5 mg | 91.5 mg | 91.5 mg | — |
| HAp of 2 part | 183.0 mg | 183.0 mg | 183.0 mg | 183.0 mg | — |
| HAp of 1 part | 0.0 mg | 0.0 mg | 0.0 mg | 0.0 mg | 91.5 mg |

Example 7

0% (span83)-0.1% (PVA)-10% (PLAG(50/50))-8 mg(HAP)

Figure 16:
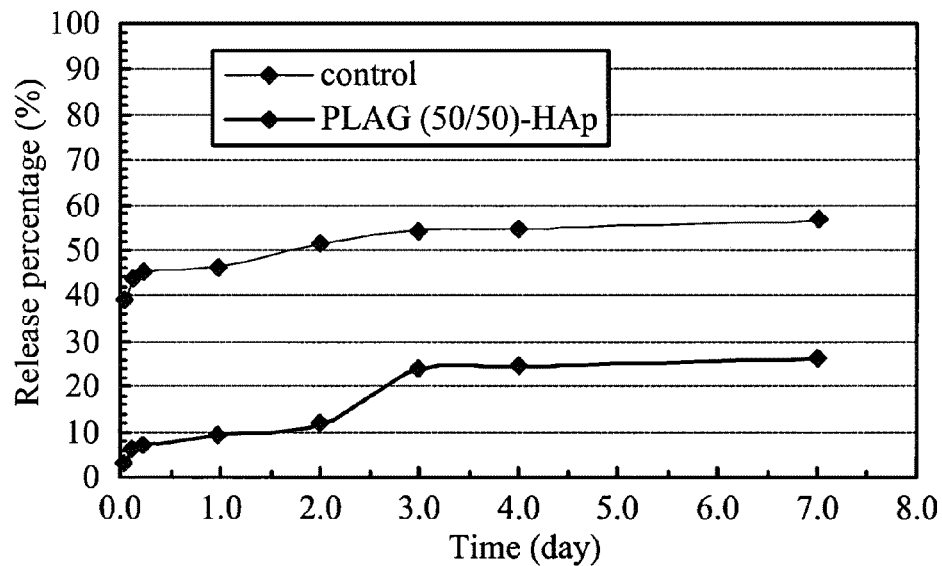
FIG. 16 shows the HAp reducing the release rate of BSA in Example 7.

8 mg of the self-made HAp and 1 mg of BSA was added to 250 μl of PBS buffer, and then stirred for 5 min to form a BSA/HAP/PBS first solution. 0.25 g of the PLGA (50/50) was dissolved in 2.5 ml of the dichloromethane to form a 10% PLGA solution. The BSA/HAP/PBS first solution and the 10% PLGA were mixed at 1000 rpm for 15 min to form a first emulsion (w/o). The first emulsion (w/o) was added to 10 ml of the 0.1% (w/v) of PVA second solution, and then stirred at 5000 rpm for 5 min to form a second emulsion (w/o/w). After stirring for 4 hours and standing for 2 min, the supernatant of the second emulsion was obtained and centrifuged at 3000 rpm for 5 min to obtain a subphase solution. The subphase solution was again washed with dd$H_2O$ and centrifuged two times. The total subphase solutions were collected and free-dried to form the controlled release system of the invention. In a control group, no HAp was added. 50 mg of the second emulsion was added to 5 ml of PBS buffer at 37° C., and then the pH of the PBS buffer containing the second emulsion was detected at days 1, 4, 7, 11, 14, 18, 21, 25, 28, and 32. In this example, the second emulsion had an encapsulation rate of 96.5% and a production rate of 80.8%. The control group had an encapsulation rate of 96.65% and a production rate of 80.8%. The pH of the example and control group were both between 7.3 and 7.4. Referring to FIG. 16, HAp effectively decreased the burst release rate of the second emulsion.

Example 8

0% (span83)-0.1% (PVA)-10% (PLAG(65/35))-8 mg(HAp)

Figure 17:
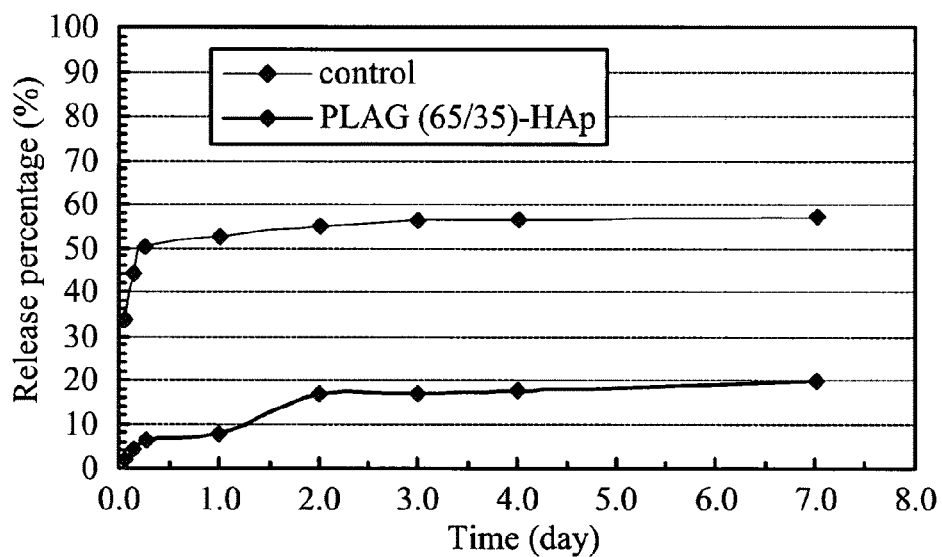
FIG. 17 shows the HAp reducing the release rate of BSA in Example 8.

The same procedure carried out in Example 7 was repeated except that 50/50 of PLAG was changed to the 65/35 of PLGA. In a control group, no HAp was added. In this example, the second emulsion had an encapsulation rate of 98.24% and a production rate of 71.2%. The control group had an encapsulation rate of 98.69% and a production rate of 80.8%. The pH of the experimental and the control group were both between 7.3 and 7.4. Referring to FIG. 17, HAp effectively decreased the burst release rate of the second emulsion.

Example 9

0% (span83)-0.1% (PVA)-10% (PLAG(85/15))-8 mg(HAp)

Figure 18:
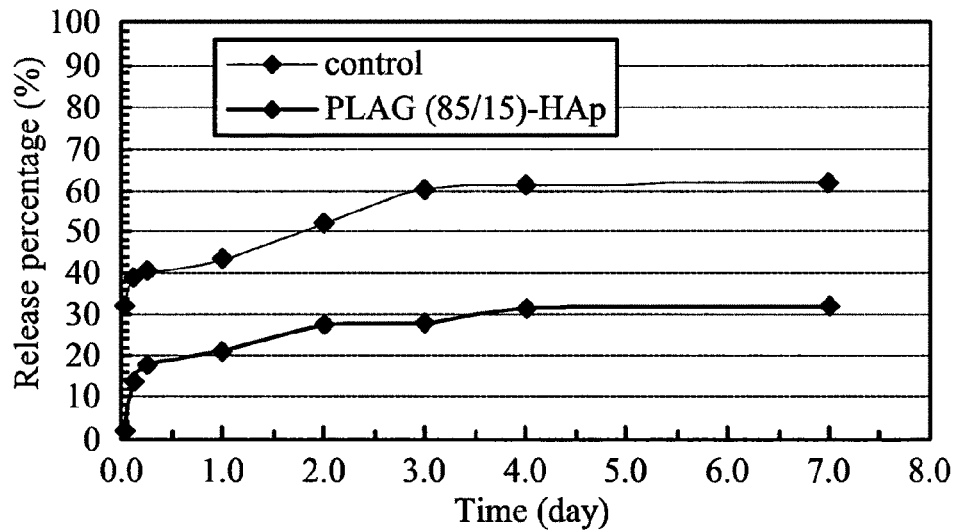
FIG. 18 shows the HAp reducing release rate of BSA in Example 9.

The same procedure carried out in Example 7 was repeated except that 50/50 of PLAG was changed to the 85/15 of PLGA. In a control group, no HAp was added. In this example, the second emulsion had an encapsulation rate of 91.12% and a production rate of 64.3%. The control group had an encapsulation rate of 98.11% and a production rate of 74.4%. The pH of the experimental and the control group were both between 7.3 and 7.4. Referring to FIG. 18, HAp effectively decreased the burst release rate of the second emulsion.

Example 10

2% (span83)-0.1% (PVA)-10% (PLAG(50/50))-8 mg(HAp)

Figure 19:
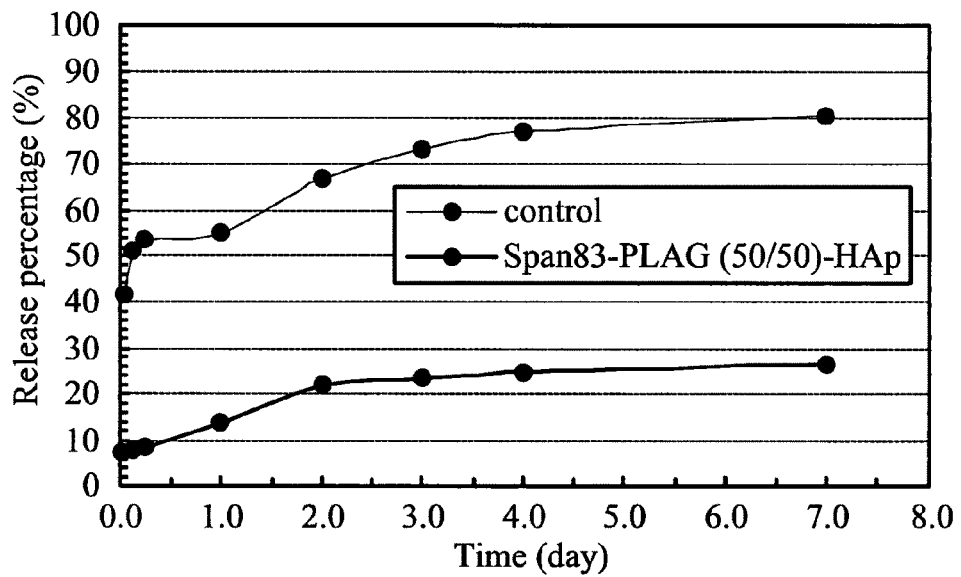
FIG. 19 shows the HAp reducing release rate of BSA in Example 10.

8 mg of the self-made HAp and 1 mg of the BSA were added to 250 µl of PBS buffer, and then centrifuged for 5 min to form a BSA/HAp/PBS first solution. 0.25 g of the 50/50 PLGA solution and 2% Span 83 was added to the 2.5 ml of the dichloromethane to form a 10% PLGA/Span 83 solution. BSA/HAp/PBS first solution and 10% PLGA solution were mixed and stirred at 1000 rpm for 15 min to form a first emulsion (w/o). The first emulsion (w/o) was added to 10 ml of 0.1% (w/v) PVA second solution with 500 rpm stirring for 5 min to form a second emulsion (w/o/w). After stirring for 4 hours and standing for 1 min, the supernatant of the second emulsion was obtained, and then the supernatant was centrifuged at 3000 rpm for 5 min to obtain a subphase solution. The original subphase solution and centrifuged subphase solution were washed with 10 ml of ddH2O for 1 min and centrifuged two times. The total subphase solutions were collected and free-dried to form the controlled release system of the invention. In a control group, no HAp was added. 50 mg of the second emulsion was added to 5 ml of PBS buffer at 37° C., and then the pH of the PBS buffer containing the second emulsion was detected at days 1, 4, 7, 11, 14, 18, 21, 25, 28, and 32. In this example, the second emulsion had an encapsulation rate of 98.7% and a production rate of 99.2%. The control group had an encapsulation rate of 99.1% and a production rate of 99.2%. The pH values of the example and control group were both between 7.3 and 7.4. Referring to FIG. 19, HAp effectively decreased the burst release rate of the second emulsion.

Example 11

2% (span83)-0.1% (PVA)-10% (PLAG(85/15))-8 mg(HAp)

Figure 20:
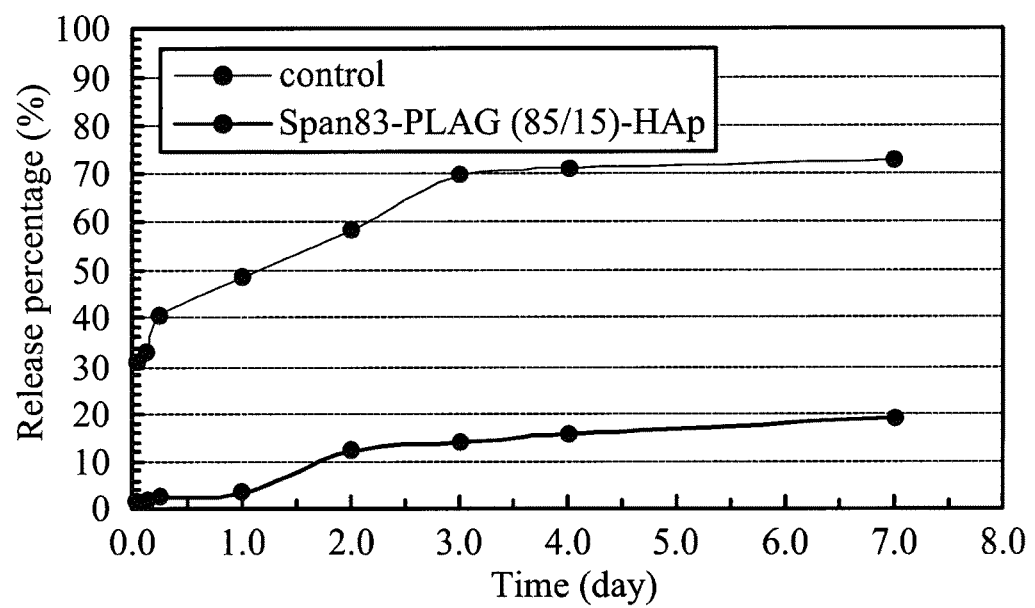
FIG. 20 shows the HAp reducing release rate of BSA in Example 11.

The same procedure carried out in Example 10 was repeated except that 50/50 of PLAG was changed to the 85/15 of PLGA. In a control group, no HAp was added. In this example, the second emulsion had an encapsulation rate of 95.9% and a production rate of 45.5%. The control group had an encapsulation rate of 96.7% and a production rate of 86.5%. The pH of the experimental and the control group were both between 7.3 and 7.4. Referring to FIG. 20, HAp effectively decreased the burst release rate of the second emulsion.

Example 12

The Analysis of 75/25 PLGA Encapsulating 5(6)-carboxyfluororescein

Figure 21:
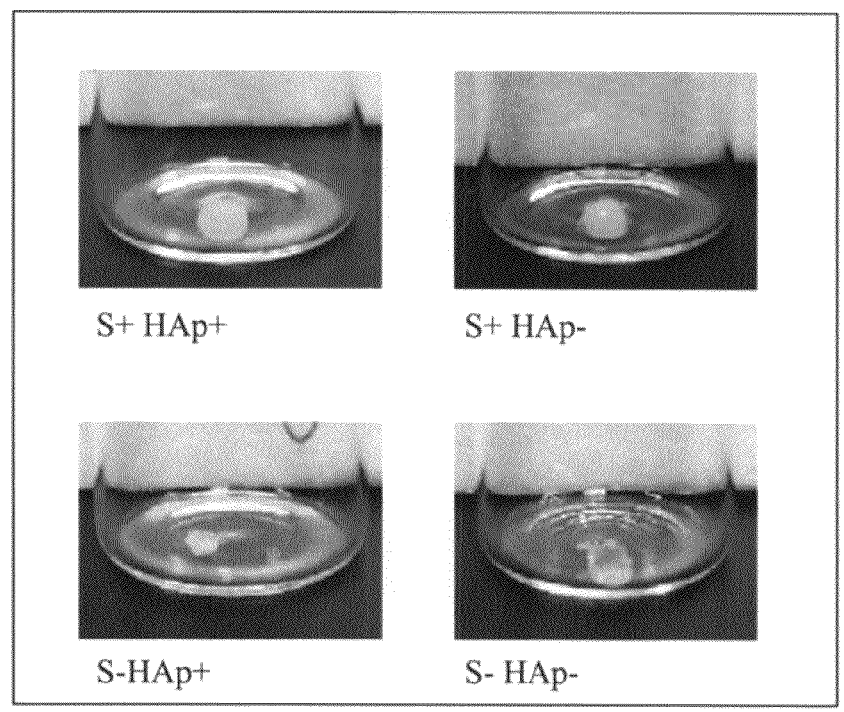
FIG. 21 shows the shape of sample of Example 12.
Figure 22:
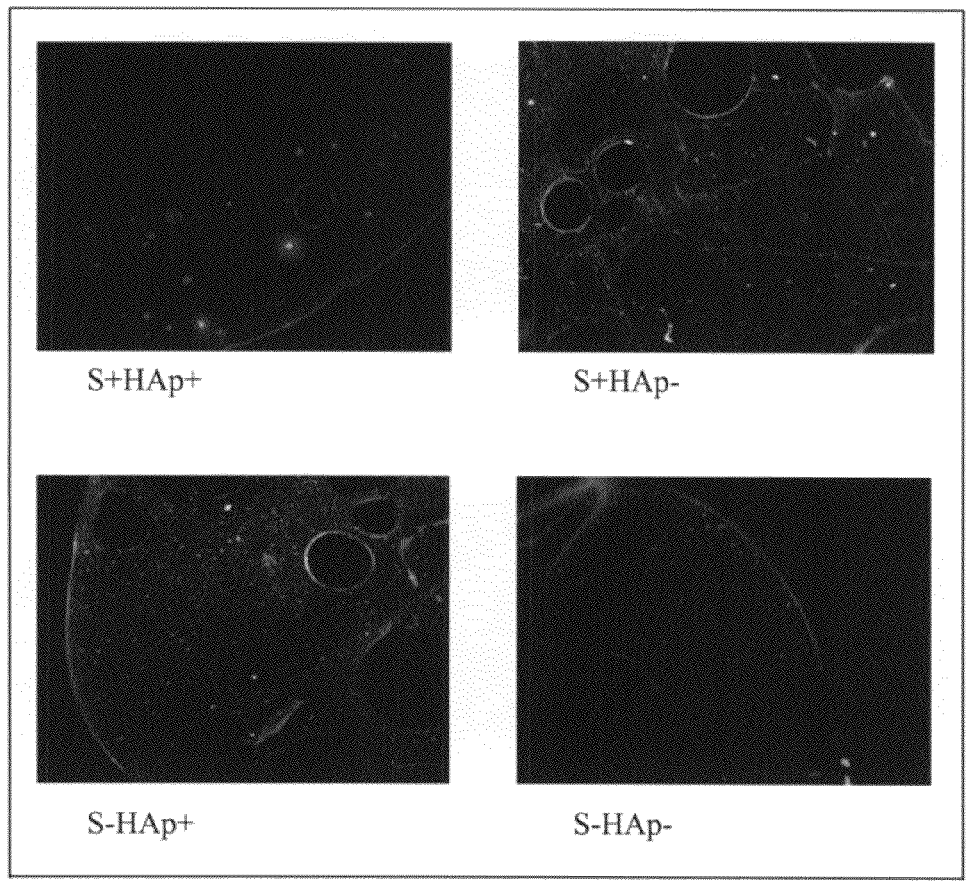
FIG. 22 shows the surfactant and HAp induced dispersion of the fluorescent material.

The example comprises four groups: (1) without surfactant and HAp (S−HAp−)group; (2) with surfactant but without HAp (S+HAp−)group; (3) without surfactant but with HAp (S−HAp+)group; (4) with surfactant and HAp (S−HAp+) group. The (1)group: 25 µl of 5(6)-carboxyfluororescein was added to 250 µl of PLGA/DCM solution with stirring for 5 min to form a mixture. The mixture was added into a mold, and the organic solvent in the mixture was removed by an air exhauster. Finally, the resulting solution was vacuum dried for 2 days. The (2)group: 25 µl of 5(6)-carboxyfluororescein and 0.1% Span 83 were added to 250 µl of PLGA/DCM solution with stirring for 5 min to form a mixture. The mixture was added into a mold, and the organic solvent in the mixture was removed by an air exhauster. Finally, the resulting solution was vacuum dried for 2 days. The (3)group: 20 g/5 ml HAp was sonicated for 15 min. After standing for 5 min, the upper ⅓ layer supernatant was obtained, and then the supernatant and 25 µl of 5(6)-carboxyfluororescein were mixed and centrifuged at for 5 min to form a pellet. The pellet was dissolved in 250 µl of PLGA solution with stirring for 5 min to form a mixture. The mixture was added into a mold, and the organic solvent in the mixture was removed by an air exhauster. Finally, the resulting solution was vacuum dried for 2 days. The (4) group: the HAp supernatant and 25 µl of 5(6)-carboxyfluororescein were mixed and centrifuged at 3000 rpm for 5 min to form a pellet. The pellet was dissolved in 250 µl of PLGA solution with stirring for 5 min to form a mixture. The mixture was added into a mold, and the organic solvent in the mixture was removed by an air exhauster. Finally, the resulting solution was vacuum dried for 2 days. The FIG. 21 shows the sample shape of the four groups. The FIG. 22 shows sliced images of the four groups from microscopy. This experiment demonstrates that the surfactant and the HAp induced the dispersion of the fluorescent material.

Example 13

The Analysis of 85/15 PLGA Encapsulating 5(6)-carboxyfluororescein

Figure 23:
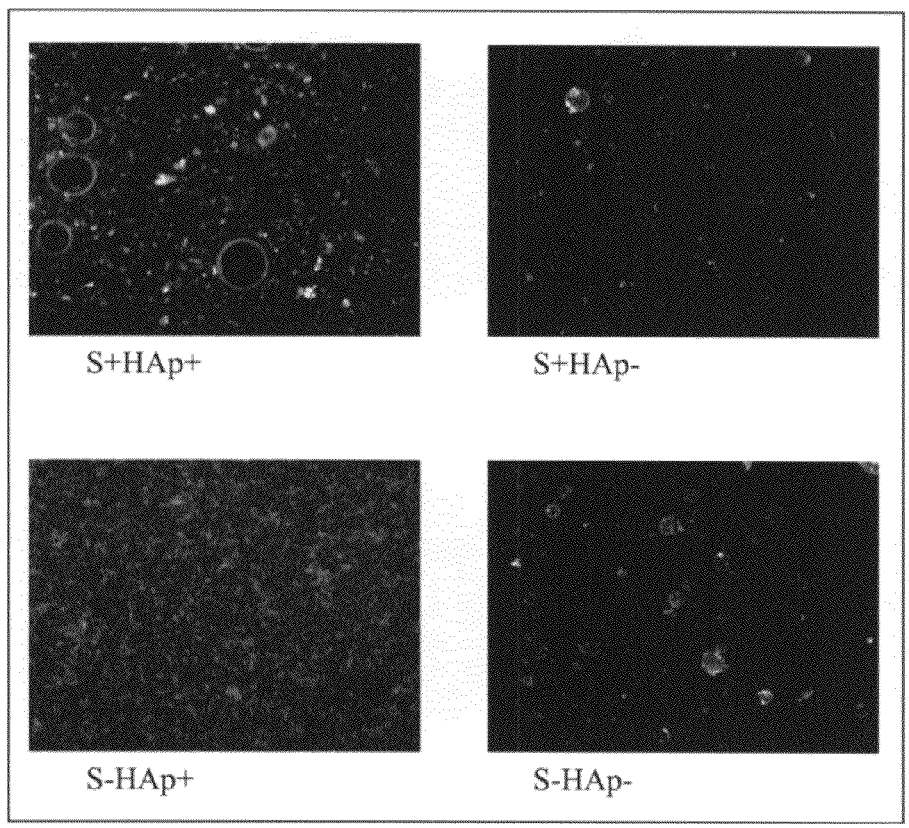
FIG. 23 shows the surfactant and HAp induced dispersion of the fluorescent material.

The same procedure carried out in Example 12 was repeated except that 75/25 PLGA was changed to the 85/15 PLGA. The FIG. 23 shows sliced images of the four groups from microscopy. This experiment demonstrates that the surfactant and the HAp induced the dispersion of the fluorescent material.

Example 14

The Effect of Excipient to rh-BMP Activity

Figure 24:
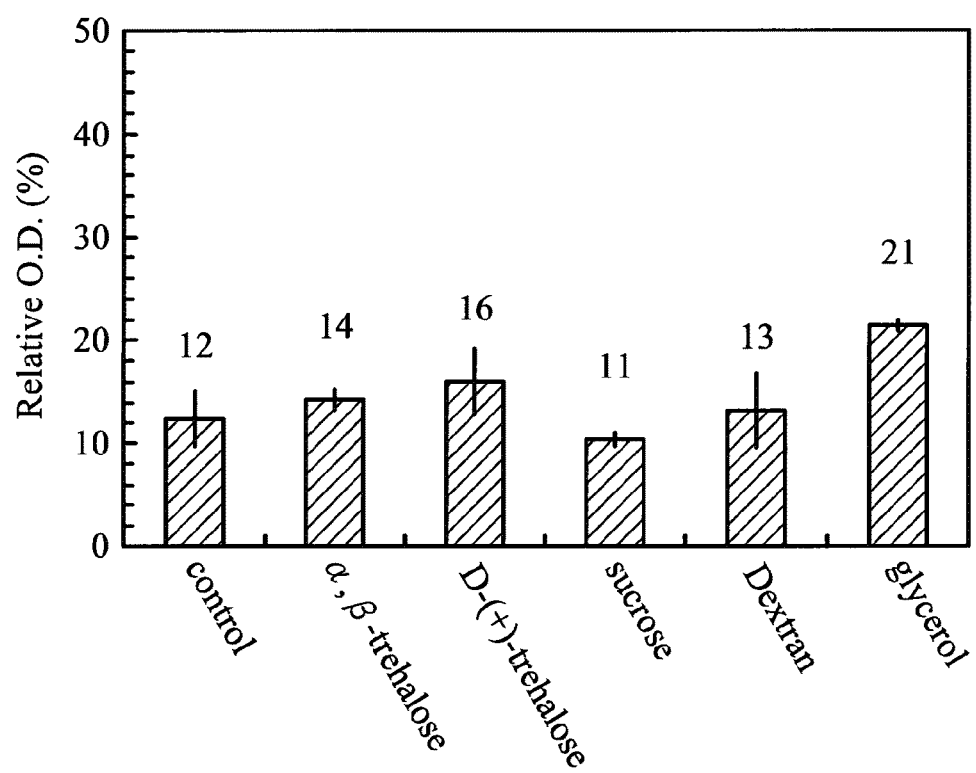
FIG. 24 shows the excipient protection of the protein activity.

This example demonstrates that the excipient can protect the protein activity according to the analysis of the excipient and rh-BMP activity. The excipient was added to 2000 pg/ml rh-BMP, and then mixed with dichloromethane for 10 min. The excipient comprises 1% α,β-Trehalose, 1% D-(+)-Trehalose, 1% sucrose, 1% glycerol, or 1% dextrin. The ratio of rh-BMP containing excipient to dichloromethane was 1:10 (vol %). In a control group, no HAp was added. Referring to FIG. 24, the vacuum drying step and organic solvent reduced the activity of the rh-BMP2, but the excipient protected the activity of the rh-BMP2.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for manufacturing a controlled release system, consisting of
   (a) providing a first solution comprising a hydrophilic agent and an alkaline material, wherein the alkaline material comprises hydroxyapatite, tricalcium phosphate, bioglass, calcium carbonate, polyamidoamine (PAMAM) dendrimer, xylitol, or combinations thereof;
   (b) providing an organic solution comprising a hydrophobic molecule;
   (c) providing a second solution comprising a hydrophilic surfactant;
   (d) mixing the first solution with the organic solution to form a first emulsion; and
   (e) mixing the first emulsion with the second solution to form a water-in-oil-in-water second emulsion containing delayed-release microsphere.

2. The method as claimed in claim 1, further comprising washing the second emulsion.

3. The method as claimed in claim 1, wherein the hydrophilic agent comprises protein, nucleic acid, or antibiotic growth factor.

4. The method as claimed in claim 1, wherein the organic solution comprises dichloromethane, chloroform, ethyl acetate, 1,4-dioxane, dimethylformamide (DMF), dimethyl sulphoxide (DMSO), toluene, or tetrahydrofuran (THF).

5. The method as claimed in claim 1, wherein the hydrophobic molecule is a biodegradable molecule.

6. The method as claimed in claim 1, wherein the hydrophobic molecule comprises phospholipids, lecithin, polylactic acid (PLA), polyglycolate, polylactide-co-glycolide (PLGA), polyglutamic acid, polycaprolactone (PCL), polyanhydrides, polyamino acid, polydioxanone, polyhydroxybutyrate, polyphophazenes, polyesterurethane, polycarbosyphenoxypropane-cosebacic acid, or polyorthosester.

7. The method as claimed in claim 1, wherein step (b) further comprises adding a hydrophobic surfactant.

8. The method as claimed in claim 7, wherein the hydrophobic surfactant comprises polyoxypropylene-polyoxyethylene copolymers, polysorbates, polyglycerol polyricinoleate, sorbitan tristearate, mono-diglycerides of fatty acid, polyglycerol stearate, sorbitan mono-stearate, sobitan monpalmitate, sodium bis(2-ethylhexyl) sulfosuccinate (AOT), polyoxyethylene-polyoxypropylene-polyoxyethylene triblock copolymers, sorbitan sesquioleate, or sorbitan monopalmitate.

9. The method as claimed in claim 1, wherein the hydrophilic surfactant comprises polyvinyl alcohol (PVA), nonylphenyl pentaethylene glycol, 4-octylphenol polyethoxylate, polyoxyethylene (20) sorbitan monooleate, PEG 200-800, sodium dodecyl sulfate (SDS), alcohol ethoxylates, alkylphenol ethoxylates, secondary alcohol ethoxylates, fatty acid ester, or alkyl polygylcosides.

10. The method as claimed in claim 1, wherein a ratio of the hydrophilic agent to the organic solution is about 1:5 to 1:13.

11. The method as claimed in claim 1, further comprising adding an excipient to the hydrophilic agent.

12. The method as claimed in claim 11, wherein the excipient comprises dextrin, α,β-trehalose, D-(+)-trehalose, sucrose, glycerol, cyclodextrin, polyhydric alcohols, or PEG.

13. The method as claimed in claim 1, wherein the temperature of steps (a) to (e) is controlled in 0 to 60° C.

14. The method as claimed in claim 1, further comprising shaping the second emulsion to form a bone scaffold, and a pH of the bone scaffold dissolved in a physiological solution in vitro for one month is about 6.5 to 8.5.

15. The method as claimed in claim 14, wherein the pH is about 7.0 to 8.0.

16. A controlled release system prepared by the method of claim 1, wherein the controlled release system has a pH of about 6.5 to 8.5, a burst release rate between about 5% and 60% at first hour and a drug encapsulation rate exceeding 80%.

17. The controlled release system as claimed in claim 16, wherein the pH is about 7.0 to 8.0.

18. The controlled release system as claimed in claim 16, wherein the drug encapsulation rate exceeds 90%.

19. The controlled release system as claimed in claim 16, wherein the controlled release system has a diameter between about 0.1 and 500 μm.

20. The controlled release system as claimed in claim 16, wherein the hydrophilic agent comprises hydrophilic compound, protein, nucleic acid, antibiotic or growth factor.

* * * * *